United States Patent

Kraatz et al.

[11] Patent Number: 4,629,732
[45] Date of Patent: Dec. 16, 1986

[54] FUNGICIDALLY ACTIVE 3-SUBSTITUTED 1-AZOLYL-3-METHYL-1-PHENOXY-BUTAN-2-ONES AND -OLS

[75] Inventors: Udo Kraatz, Leverkusen; Erich Klauke, Odenthal; Gerhard Jager, Leverkusen; Karl H. Buchel, Burscheid; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 600,581

[22] Filed: Apr. 17, 1984

Related U.S. Application Data

[63] Continuation of Ser. No. 370,754, Apr. 22, 1982, abandoned.

[30] Foreign Application Priority Data

May 15, 1981 [DE] Fed. Rep. of Germany ....... 3119390

[51] Int. Cl.$^4$ ................. A01N 43/50; A01N 43/653; C07D 233/60; C07D 249/08
[52] U.S. Cl. .................................. 514/383; 514/184; 514/399; 548/101; 548/262; 548/341; 568/43; 568/308; 568/325
[58] Field of Search ...................... 548/262, 341, 101; 424/245, 269, 273 R; 514/184, 383, 399

[56] References Cited

U.S. PATENT DOCUMENTS

| | | | |
|---|---|---|---|
| 4,123,542 | 10/1978 | Walker | 548/341 |
| 4,154,842 | 5/1979 | Kramer et al. | 548/262 |
| 4,215,127 | 7/1980 | Rogers et al. | 548/262 |
| 4,399,143 | 8/1983 | Yokomichi et al. | 548/262 |
| 4,406,909 | 9/1983 | Kramer et al. | 548/262 |

FOREIGN PATENT DOCUMENTS 0049111 4/1982 European Pat. Off.
7724264 3/1978 France.

OTHER PUBLICATIONS

Burger, Medicinal Chemistry, (Second Edition, New York, 1960), p. 1055.
Horsfall, Fungicides and Their Action, (Waltham, Mass., 1945), pp. 151–152.

*Primary Examiner*—Alton D. Rollins
*Attorney, Agent, or Firm*—Sprung Horn Kramer & Woods

[57] ABSTRACT

New 3-substituted 1-azolyl-3-methyl-1-phenoxy-butan-2-ones and -ols of the general formula

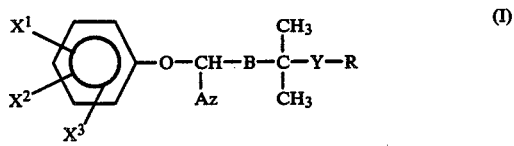

in which
Az represents 1,2,4-triazol-1-yl, 1,2,4-triazol-4-yl or imidazol-1-yl,
B represents the keto group or the CH(OH) group,
Y represents oxygen or sulphur,
R represents halogenoalkyl, optionally substituted phenyl or optionally substituted benzyl, or provided Y represents sulphur, may represent alkyl and
$X^1$, $X^2$ and $X^3$ are selected independently and each represent hydrogen, halogen, alkyl, halogenoalkyl, alkoxy, alkylthio, alkylsulphonyl, nitro, cyano, alkoxycarbonyl or optionally substituted phenyl, are obtained if halogenoether ketones are reacted with 1,2,4-triazole or imidazole in the presence of a diluent and of an acid-binding agent, and, if appropriate, the keto derivatives thus obtained are reduced. The compounds, as such or as their acid-addition salts or metal-salt complexes, have fungicidal activity, for example against those fungi which cause powdery mildew diseases or cause rice diseases.

9 Claims, No Drawings

FUNGICIDALLY ACTIVE 3-SUBSTITUTED 1-AZOLYL-3-METHYL-1-PHENOXY-BUTAN-2-ONES AND -OLS

This is a continuation of application Ser. No. 370,754, filed Apr. 22, 1982, abandoned.

The present invention relates to certain new 3-substituted 1-azolyl-3-methyl-1-phenoxy-butan-2-ones and -ols, to a process for their preparation and to their use as fungicides.

It has already been disclosed that 1-azolyl-3,3-dimethyl-1-phenoxy-butan-2-ones and -ols have generally good fungicidal properties (see U.S. Pat. Nos. 3,912,752; 4,147,791; 4,048,318; 3,952,002 and 3,898,341). However, the action of these compounds is not always completely satisfactory, particularly when small quantities and low concentrations are used; the same applies to compounds disclosed in U.S. Pat. No. 4,215,127.

The present invention now provides, as new compounds, the 3-substituted 1-azolyl-3-methyl-1-phenoxy-butan-2-ones and -ols of the general formula

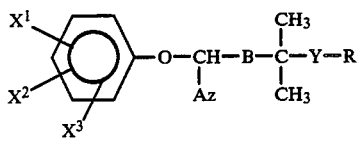

in which
- Az represents 1,2,4-triazol-1-yl, 1,2,4-triazol-4-yl or imidazol-1-yl,
- B represents the keto group or the CH(OH) group,
- Y represents oxygen or sulphur,
- R represents halogenoalkyl, optionally substituted phenyl or optionally substituted benzyl, or, provided Y represents sulphur, may represent alkyl, and
- $X^1$, $X^2$ and $X^3$ are selected independently and each represents hydrogen, halogen, alkyl, halogenoalkyl, alkoxy, alkylthio, alkylsulphonyl, nitro, cyano, alkoxycarbonyl or optionally substituted phenyl, and the physiologically tolerated acid-addition salts and metal-salt complexes thereof.

Those compounds of the formula (I) in which B represents the CH(OH) group have two asymmetric carbon atoms; they can therefore be present as two geometrical isomers (threo and erythro form), which can be produced in varying proportions. They are present as optical isomers in both cases.

The invention also provides a process for the preparation of a 3-substituted 1-azolyl-3-methyl-1-phenoxy-butan-2-one or -ol of the formula (I), in which a halogenoether ketone of the general formula

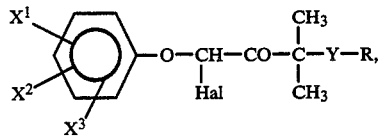

in which
- Hal represents halogen, preferably chlorine or bromine, and
- R, $X^1$, $X^2$, $X^3$ and Y have the meanings given above, is reacted with 1,2,4-triazole or imidazole in the presence of a diluent and in the presence of an acid-binding agent, and, if appropriate, the resulting keto derivative of the general formula

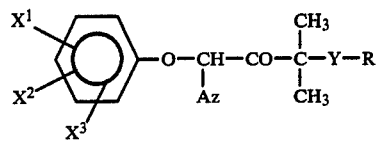

in which
- Az, R, $X^1$, $X^2$, $X^3$ and Y have the meanings given above, is reduced.

An acid or a metal salt can subsequently be added onto the resulting compound of the formula (I), if necessary. In some cases, it proves to be advantageous to obtain the compounds of the formula (I) in pure form via their salts.

The new 3-substituted 1-azolyl-3-methyl-1-phenoxy-butan-2-ones and -ols of the formula (I) have powerful fungicidal properties. In this context, the compounds according to the invention surprisingly exhibit a better fungicidal action than the 1-azolyl-3,3-dimethyl-1-phenoxy-butan-2-ones and -ols which are known from the state of the art and are similar compounds chemically and with respect to their action.

In addition, the new 3-substituted 1-azolyl-3-methyl-1-phenoxy-butan-2-ones and -ols of the formula (I) are interesting intermediate products for the preparation of further active compounds for plant protection. Thus, by appropriate reaction, functional derivatives of the keto group can be obtained, for example oximes, oxime-ethers, hydrazones and ketals. In addition, the compounds of the formula (I) can be converted in the customary manner, at the hydroxyl group, into the corresponding ethers, or acyl or carbamoyl derivatives can be obtained by reaction with, for example, acyl halides or carbamoyl chlorides, in a manner which is in principle known.

The compounds according to the invention thus represent a substantial enrichment of the art.

Formula (I) gives a general definition of the 3-substituted 1-azolyl-3-methyl-1-phenoxy-butan-2-ones and -ols according to the invention. Preferably, in this formula,
- R represents halogenoalkyl having 1 to 4 carbon atoms and 1 to 5 identical or different halogen atoms, or optionally substituted phenyl or benzyl, the phenyl substituent in either case being selected from halogen, alkyl, alkoxy and alkylthio each having 1 to 4 carbon atoms, halogenoalkyl, halogenoalkoxy and halogenoalkylthio, each having 1 to 4 carbon atoms and 1 to 5 identical or different halogen atoms, nitro, cyano, alkoxycarbonyl having 1 to 4 carbon atoms in the alkyl part, and phenyl which is optionally substituted by halogen; or provided Y represents sulphur, R may represent straight-chain or branched alkyl having 1 to 6 carbon atoms,
- $X^1$ represents hydrogen, halogen, alkyl, alkoxy, alkylthio or alkylsulphonyl each having 1 to 4 carbon atoms, halogenoalkyl having 1 to 4 carbon atoms and 1 to 5 identical or different halogen atoms, nitro, cyano, alkoxycarbonyl having 1 to 4 carbon atoms in the alkyl part, or phenyl which is optionally substituted by halogen, X² represents hydrogen, halogen, alkyl, alkoxy, alkylthio or alkylsulphonyl each having 1 to 4 carbon atoms, halogenoalkyl having 1 to 4 carbon atoms and 1 to 5 identical or different halogen atoms, nitro, cyano, alkoxycarbonyl having 1 to 4 carbon atoms in the alkyl part, or phenyl which is optionally substituted by halogen, and X³ represents hydrogen, halogen, alkyl, alkoxy or alkylthio each having 1 to 4 carbon atoms or halogenoalkyl having 1 to 4 carbon atoms and 1 to 5 identical or different halogen atoms.

Those compounds of the formula (I) are particularly preferred in which

R represents halogenoalkyl having 1 to 2 carbon atoms and 1 to 5 identical or different halogen atoms (especially phenyl or benzyl, the or phenyl substituent being in either case selected from fluorine, chlorine, methyl, ethyl, isopropyl, tert.-butyl, methoxy, methylthio, trifluoromethyl, trifluoromethoxy, trifluoromethylthio, nitro, cyano and phenyl which is optionally substituted by fluorine and/or chlorine; or R may represent straight-chain or branched alkyl having 1 to 4 carbon atoms, provided Y represents sulphur, X¹ represents hydrogen, fluorine, chlorine, bromine, iodine, methyl, ethyl, isopropyl, tert.-butyl, methoxy, methylthio, methylsulphonyl, trifluoromethyl, nitro, cyano, methoxycarbonyl, ethoxycarbonyl or phenyl which is optionally substituted by fluorine and/or chlorine, X² represents hydrogen, fluorine, chlorine, methyl, ethyl, isopropyl, tert.-butyl, methoxy, methylthio and trifluoromethyl, and X³ represents hydrogen, fluorine, chlorine or methyl.

If, for example, 1,3-bis-(4-chlorophenoxy)-1-bromo-3-methyl-butan-2-one and 1,2,4-triazole are used as the starting materials, the course of the reaction can be represented by the following equation:

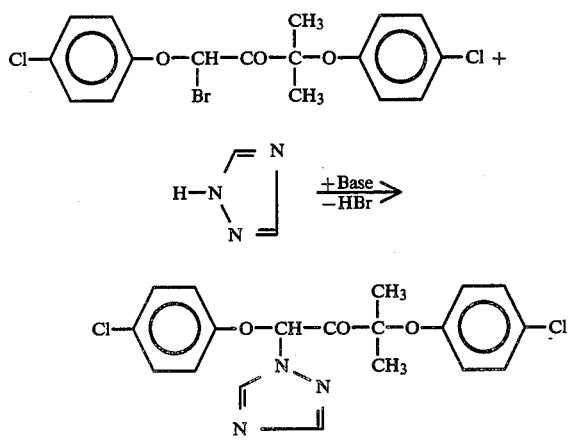

If, for example, 1,3-bis-(4-chlorophenoxy)-3-methyl-1-(1,2,4-triazol-1-yl)-butan-2-one and sodium borohydride are used as the starting materials, the course of the reaction can be represented by the following equation:

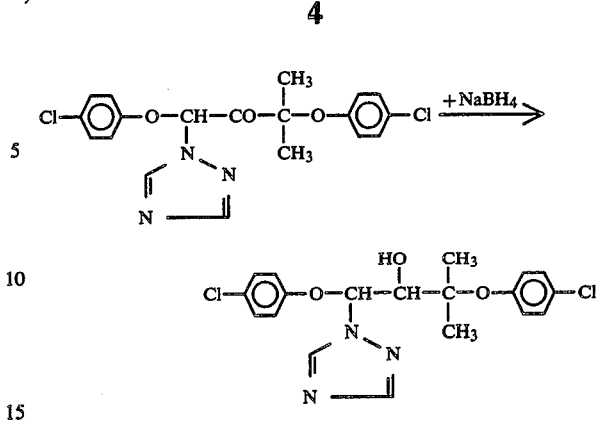

Formula (II) gives a general definition of the halogenoether ketones to be used as starting materials in carrying out the process according to the invention. In this formula, R, X¹, X², X³ and Y preferably represent those radicals which have already been mentioned, in connection with the description of the compounds of the formula (I), as being preferred for these substituents.

The halogenoether ketones of the formula (II) have not hitherto been disclosed in the literature. However, they can be obtained by known processes in which, for example, known phenols of the general formula

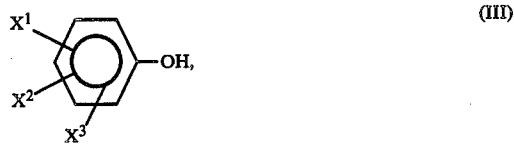

in which

X¹, X² and X³ have the meanings given above, are reacted with a halogenoketone of the general formula

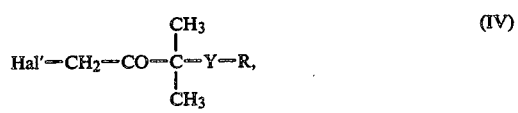

in which

Y and R have the meanings given above and

Hal' represents chlorine or bromine.

The active hydrogen atom which still remains is then replaced by halogen in a customary manner (see, also, the preparative examples). If appropriate, the halogenoether ketones of the formula (II) can be directly further reacted without isolation.

The halogenoketones of the formula (IV) have not hitherto been disclosed in the literature. However, they form the subject of United States Application Ser. No. 328,871, filed Dec. 8, 1981, abandoned. They are obtained by a process in which ketones of the general formula

in which

R and Y have the meaning given above, are reacted with chlorine or bromine in the presence of an inert organic solvent, for example ether or a chlorinated or non-chlorinated hydrocarbon, at room temperature, or with a customary chlorinating agent, for example sulphuryl chloride, at from 20° to 60° C.

Some of the ketones of the formula (V) are known (see, for example, U.S. Pat. No. 3,937,738), and some of them form the subject of U.S. Application Ser. No. 328,871, filed Dec. 8, 1981, supra. They can be obtained by the process given in the reference, for example, by reacting keto derivatives of the general formula

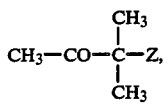
(VI)

in which

Z represents chlorine, bromine or the group

wherein $R^1$ represents alkyl having 1 to 4 carbon atoms or optionally substituted phenyl, with compounds of the formula

 (VII), in which

R and Y have the meanings given above and

M represents an alkali metal, preferably sodium and potassium, or hydrogen, in the presence of an organic solvent, for example xylene, glycol or dimethylformamide, and, if appropriate, in the presence of an acid-binding agent, for example sodium carbonate, at a temperature between 80° and 150° C.; or by reacting, for example, isopropyl methyl ketone with sulphenyl chlorides, in a customary manner.

The derivatives of the formula (VI) are known and can be obtained in a generally known manner.

The compounds of the formula (VII) are generally known compounds of organic chemistry and are employed in situ, if appropriate.

Inert organic solvents are suitable as diluents for the reaction according to the present invention. These solvents include, as preferences, ketones, such as diethyl ketone and, in particular, acetone and methyl ethyl ketone; nitriles, such as propionitrile and, in particular, acetonitrile; alcohols, such as ethanol or isopropanol; ethers, such as tetrahydrofuran or dioxane; benzene; toluene; formamides, such as, in particular, dimethylformamide; and halogenated hydrocarbons.

The reaction according to the invention is carried out in the presence of an acid-binding agent. Any of the inorganic or organic acid-binding agents which can customarily be used can be added, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylamine and N,N-dimethylbenzylamine, and furthermore pyridine and diazabicyclooctane. An appropriate excess of azole is preferably used.

The reaction temperatures can be varied within a relatively wide range. In general, the reaction is carried out at between 20° and 150° C., preferably at from 60° to 120° C. When a solvent is present, the reaction is advantageously carried out at the boiling point of the particular solvent.

In carrying out the process according to the invention, 2 to 4 mols of azole and 1 to 4 mols of acid-binding agent are preferably employed per mol of the compound of the formula (II). To isolate the compounds of the formula (I), the solvent is distilled off, and the residue is taken up with an organic solvent and washed with water. The organic phase is dried over sodium sulphate and freed from solvent in vacuo. The residue is purified by distillation or recrystallization, or by salt formation and recrystallization.

The reduction according to the invention may be effected in a customary manner, according to known methods, for example by reaction with a complex hydride, if appropriate in the presence of a diluent, or by reaction with aluminum isopropylate in the presence of a diluent.

If a complex hydride is used, a polar organic solvent is suitable as the diluent for the reaction according to the invention. Such solvents include, as preferences, alcohols, such as methanol, ethanol, butanol and isopropanol, and ethers, such as diethyl ether or tetrahydrofuran. In general, the reaction is carried out at from 0° to 30° C., preferably at from 0° to 20° C. For this reaction, about 1 mol of a complex hydride, such as sodium borohydride or lithium alanate, is employed per mol of the ketone of the formula (Ia). To isolate the resultant compound of the formula (I), the residue is taken up in dilute hydrochloric acid, and the solution is then rendered alkaline and extracted with an organic solvent. Further working-up is effected in a customary manner.

If aluminum isopropylate is used, an alcohol, such as isopropanol, or an inert hydrocarbon, such as benzene, is a preferred diluent for the reaction according to the invention. Once again, the reaction temperatures can be varied within a relatively wide range; in general, the reaction is carried out at between 20° and 120° C., preferably at from 50° to 100° C.

To carry out the reaction, about 0.3 to 2 mols of aluminum isopropylate are preferably employed per mole of the ketone of the formula (Ia). To isolate the resultant compound of the formula (I), the excess solvent is removed in vacuo and the resulting aluminum compounds are decomposed with dilute sulphuric acid or sodium hydroxide solution. Further working-up is effected in a customary manner.

The following are preferred acids for the preparation of physiologically tolerated acid-addition salts of the compounds of the formula (I): hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The acid-addition salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metals of main groups II to IV and of subgroups I and II and IV to VIII are preferably used for the preparation of metal-salt complexes of the compounds of the formula (I), examples of metals which may be mentioned being copper, zinc, manganese, magnesium, tin, iron and nickel. Preferred anions of the salts are those which are derived from the following acids: hydrogen halide acids (for example hydrochloric acid and hydrobromic acid), phosphoric acid, nitric acid and sulphuric acid.

The metal-salt complexes of the compounds of the formula (I) can be obtained in a simple manner by customary processes, for example by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, thus, for combating Erysiphe species, for example against the powdery mildew of barley or cereal causative organism (*Erysiphe graminis*) and the powdery mildew of cucumber causative organism (*Erysiphe cichoracearum*), or for combating Podosphaera species, for example against the powdery mildew of apple causative organism (*Podosphaera leucotricha*); and in addition for combating rice disease causative organisms, for example *Pellicularia sasakii*.

When used in appropriate quantities, the substances according to the invention also exhibit plant growth-regulating properties.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans or fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.0001 to 0.02% by weight, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

(a)
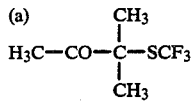

334 g of methyl isopropyl ketone in 1.2 liters of methylene chloride were initially introduced into a narrow stirred vessel equipped with a condenser. 220 g of trifluoromethane-sulphenyl chloride were introduced, at room temperature in the course of 4 hours, through an inlet tube extending to the bottom of the vessel. The reaction mixture was allowed to stand overnight. It was then distilled. 242 g (80.7% of theory) of crude 3-methyl-3-trifluoromethylthio-butan-2-one were obtained and purified by fractional distillation: boiling point: 60° C./50 mbar and refractive index $n_D^{20}=1.4030$.

(b)
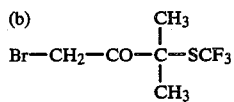

3-Methyl-3-trifluoromethylthio-butan-2-one was dissolved in chloroform and bromine was added dropwise at 20° C. at such a rate that decolorization occurred continuously. Addition was stopped when the color persisted, the reaction mixture was further stirred at 40° C. 1-Bromo-3-methyl-3-trifluoromethylthio-butan-2-one of boiling point 56° C./0.4 mbar was obtained in a yield of 85%.

(c)
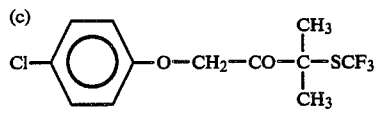

26 g (0.21 mol) of 4-chlorophenol and 42 g (0.3 mol) of potassium carbonate were introduced into 250 ml of acetone. 53 g (0.2 mol) of 1-bromo-3-methyl-3-trifluoromethylthio-butan-2-one in 50 ml of acetone were slowly added dropwise to the mixture, under reflux. After the end of the addition, the mixture was stirred under reflux for 12 hours and was filtered, and the filtrate was concentrated. The residue was taken up in 500 ml of methylene chloride, the solution was extracted by shaking with water and sodium bicarbonate solution, and the organic phase was dried over sodium sulphate and concentrated. The residue was distilled in vacuo. 45.3 g (73% of theory) of 1-(4-chlorophenoxy)-3-methyl-3-trifluoromethylthio-butan-2-one of boiling point 105° C./0.4 mbar were obtained.

(d)
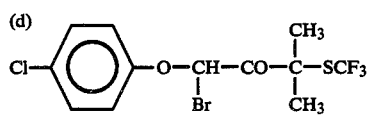

45 g (0.15 mol) of 1-(4-chlorophenoxy)-3-methyl-3-trifluoromethylthio-butan-2-one were dissolved in 150 ml of chloroform, and 7.5 ml (0.15 mol) of bromine were added dropwise at 20° C. at such a rate that decolorization occurred continuously. After the end of the addition, the reaction mixture was further stirred at 40° C. for 20 minutes and was then introduced into water. The mixture was extracted with chloroform and concentrated at 40° C. 1-Bromo-1-(4-chlorophenoxy)-3-methyl-3-trifluoromethylthio-butan-2-one was obtained quantitatively and was directly further reacted.

(e)
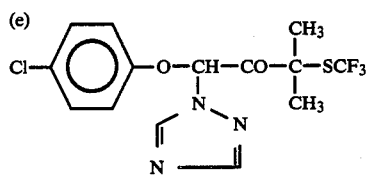
(1)

29 g (0.075 mol) of crude 1-bromo-1-(4-chlorophenoxy)-3-methyl-3-trifluoromethylthio-butan-2-one and 16 g (0.25 mol) of 1,2,4-triazole in 150 ml of acetonitrile were heated under reflux for 1 hour. Thereafter, the mixture was concentrated and the residue was taken up with methylene chloride/water. The organic phase was separated off, dried over sodium sulphate and concentrated again. The oil residue was chromatographed. 10.4 g (37% of theory) of 1-(4-chlorophenoxy)-3-methyl-1-(1,2,4-triazol-1-yl)-3-trifluoromethylthio-butan-2-one of melting point 66° C. were obtained.

Example 2

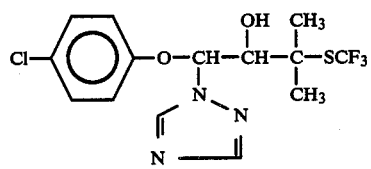
(2)

10 g (0.026 mol) of 1-(4-chlorophenoxy)-3-methyl-1-(1,2,4-triazol-1-yl)-3-trifluoromethylthio-butan-2-one (Example 1) were dissolved in 100 ml of methanol and 1 g (0.025 mol) of sodium borohydride was added in portions to the solution. The reaction mixture was further stirred at room temperature for 30 minutes and was thereafter introduced into water. The mixture was extracted with methylene chloride, and the organic phase was dried over sodium sulphate and concentrated in vacuo. The residue crystallized after a short time. 9.5 g (95% of theory) of 1-(4-chlorophenoxy)-3-methyl-1-(1,2,4-triazol-1-yl)-3-trifluoromethylthio-butan-2-ol of melting point 85°–87° C. were obtained.

The following compounds of the general formula

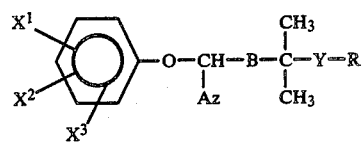  (I)

were obtained in a manner analogous to that in Example 1 or 2.

| Compound No. | $X^1$ | $X^2$ | $X^3$ | Az | B | —YR | Melting point (°C.) |
|---|---|---|---|---|---|---|---|
| 3 | 4-Cl | H | H | 1,2,4-Triazol-1-yl | CO | —O—⟨C₆H₄⟩—Cl | Resin |
| 4 | 4-Cl | H | H | 1,2,4-Triazol-1-yl | CO | —O—⟨C₆H₃(Cl)⟩—Cl | Resin |
| 5 | 4-Cl | H | H | 1,2,4-Triazol-1-yl | CO | —O—⟨C₆H₃(CH₃)⟩—Cl | Resin |
| 6 | 4-Cl | H | H | 1,2,4-Triazol-1-yl | CO | —O—⟨C₆H₄⟩—⟨C₆H₅⟩ | 110 |
| 7 | 2-Cl | 4-Cl | H | 1,2,4-Triazol-1-yl | CO | —SCF₃ | 105 |
| 8 | 4-CH₃ | 4-Cl | H | 1,2,4-Triazol-1-yl | CO | —SCF₃ | 90 |
| 9 | 4-Cl | H | H | 1,2,4-Triazol-4-yl | CO | —O—⟨C₆H₄⟩—⟨C₆H₅⟩ | Resin |
| 10 | 2-Cl | 4-Cl | H | 1,2,4-Triazol-4-yl | CO | —SCF₃ | 156 |
| 11 | 2-CH₃ | 4-Cl | H | 1,2,4-Triazol-4-yl | CO | —SCF₃ | 141 |
| 12 | 2-Cl | 4-Cl | H | 1,2,4-Triazol-4-yl | CO | —O—⟨C₆H₁₀⟩—Cl | 161 |
| 13 | 4-Cl | H | H | 1,2,4-Triazol-1-yl | CH(OH) | —O—⟨C₆H₄⟩—Cl | Resin |
| 14 | 2-Cl | 4-Cl | H | 1,2,4-Triazol-1-yl | CH(OH) | —SCF₃ | 91 |
| 15 | 2-Cl | 4-Cl | H | 1,2,4-Triazol-1-yl | CH(OH) | —O—⟨C₆H₄⟩—Cl | Resin |
| 16 | 4-Cl | H | H | Imidazol-1-yl | CO | —O—⟨C₆H₄⟩—Cl | Resin |
| 17 | 4-Cl | H | H | Imidazol-1-yl | CO | —SCF₃ | 88 |

-continued

| Compound No. | $X^1$ | $X^2$ | $X^3$ | Az | B | —YR | Melting point (°C.) |
|---|---|---|---|---|---|---|---|
| 18 | 4-Cl | H | H | Imidazol-1-yl | CO | 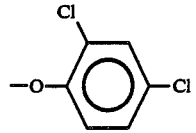 | Resin |
| 19 | 4-Cl | H | H | Imidazol-1-yl | CO | 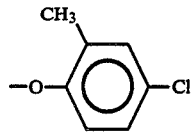 | Resin |
| 20 | 4-Cl | H | H | Imidazol-1-yl | CO | 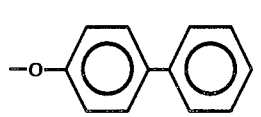 | Resin |
| 21 | 2-Cl | 4-Cl | H | Imidazol-1-yl | CO | —SCF$_3$ | 105–07 |
| 22 | 2-CH$_3$ | 4-Cl | H | Imidazol-1-yl | CO | —SCF$_3$ | Oil |
| 23 | 2-Cl | 4-Cl | H | Imidazol-1-yl | CO | 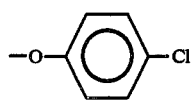 | Resin |
| 24 | 4-Cl | H | H | Imidazol-1-yl | CO | 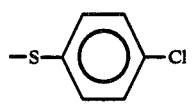 | 150 |
| 25 | 4-Cl | H | H | Imidazol-1-yl | CH(OH) | —SCF$_3$ | 145 |
| 26 | 4-Cl | H | H | Imidazol-1-yl | CH(OH) | 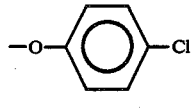 | Resin |
| 27 | 4-Cl | H | H | Imidazol-1-yl | CH(OH) | 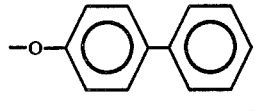 | 163 |
| 28 | 4-Cl | H | H | Imidazol-1-yl | CH(OH) | 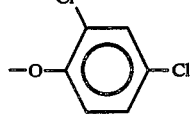 | Resin |
| 29 | 2-Cl | 4-Cl | H | Imidazol-1-yl | CH(OH) | —SCF$_3$ | 137–39 |
| 30 | 4-Cl | H | H | Imidazol-1-yl | CH(OH) | 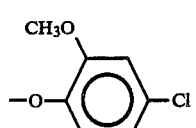 | Resin |
| 31 | 4-Cl | H | H | Imidazol-1-yl | CH(OH) | 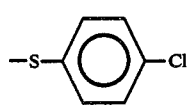 | 145–147 |
| 32 | 4-Cl | H | H | 1,2,4-Triazol-1-yl | CO | 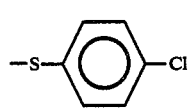 | 116 |

-continued

| Compound No. | X¹ | X² | X³ | Az | B | —YR | Melting point (°C.) |
|---|---|---|---|---|---|---|---|
| 33 | 4-Cl | H | H | 1,2,4-Triazol-4-yl | CO | 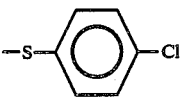 —S—⟨C₆H₄⟩—Cl | 156 |
| 34 | 2-Cl | 4-Cl | H | Imidazol-1-yl | CO | 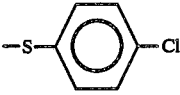 —S—⟨C₆H₄⟩—Cl | 133 |
| 35 | 2-Cl | 4-Cl | H | 1,2,4-Triazol-1-yl | CO | 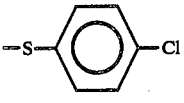 —S—⟨C₆H₄⟩—Cl | 90–94 |
| 36 | 2-Cl | 4-Cl | H | 1,2,4-Triazol-4-yl | CO | 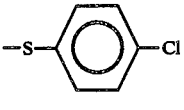 —S—⟨C₆H₄⟩—Cl | Resin |
| 37 | 4-F | H | H | Imidazol-1-yl | CO | —SCF₃ | 68–70 |
| 38 | 4-Cl | H | H | 1,2,4-Triazol-1-yl | CH(OH) | 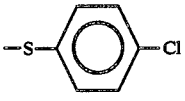 —S—⟨C₆H₄⟩—Cl | 45 |
| 39 | 2-CH₃ | 4-Cl | H | Imidazol-1-yl | CH(OH) | —SCF₃ | 115 |
| 40 | 4-F | H | H | Imidazol-1-yl | CH(OH) | —SCF₃ | 120 |
| 41 | 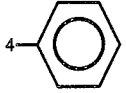 4-⟨C₆H₅⟩ | H | H | 1,2,4-Triazol-1-yl | CH(OH) | —SCF₃ | 98–100 |
| 42 | 2-Cl | 4-Cl | H | Imidazol-1-yl | CH(OH) |  —S—⟨C₆H₄⟩—Cl | resin |
| 43 | 4-F | H | H | Imidazol-1-yl | CO | 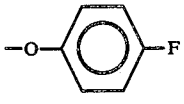 —O—⟨C₆H₄⟩—F | resin |
| 44 | 4-F | H | H | 1,2,4-Triazol-1-yl | CO | 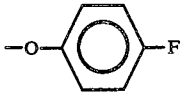 —O—⟨C₆H₄⟩—F | 78–80 |
| 45 | 4-F | H | H | Imidazol-1-yl | CH(OH) | 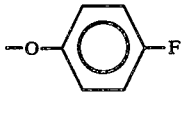 —O—⟨C₆H₄⟩—F | resin |
| 46 | 4-F | H | H | 1,2,4-Triazol-1-yl | CH(OH) |  —O—⟨C₆H₄⟩—F | resin |
| 47 | 4-Cl | H | H | Imidazol-1-yl | CO |  —O—⟨C₆H₄⟩—F | resin |

-continued

| Compound No. | X¹ | X² | X³ | Az | B | —YR | Melting point (°C.) |
|---|---|---|---|---|---|---|---|
| 48 | 4-Cl | H | H | 1,2,4-Triazol-1-yl | CO | 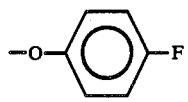 | 89 |
| 49 | 4-Cl | H | H | 1,2,4-Triazol-4-yl | CO | 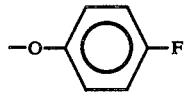 | 80–85 |
| 50 | 4-Cl | H | H | 1,2,4-Triazol-1-yl | CH(OH) | 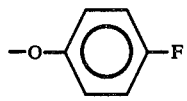 | resin |
| 51 | 4-Cl | H | H | 1,2,4-Triazol-1-yl | CO | 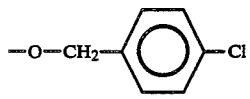 | 82–84 |
| 52 | 4-Cl | H | H | 1,2,4-Triazol-4-yl | CO | 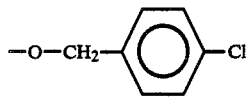 | resin |

USE EXAMPLES

The fungicidal activity of the compounds of this invention is illustrated by the following biotest examples.

In these examples, the compounds according to the present invention are each identified by the number (given in brackets) from the preparative examples and table.

The compounds indicated below were employed as comparative substances in the examples which follow:

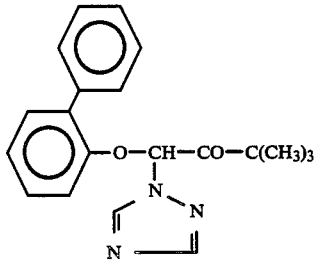
(A)

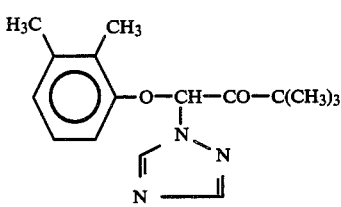
(B)

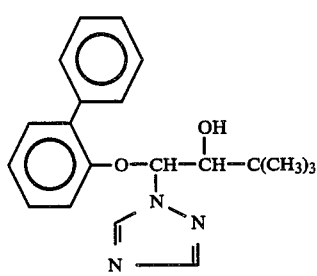
(C)

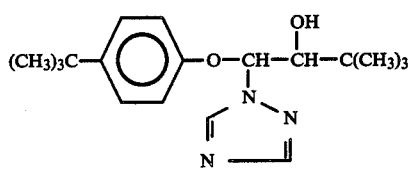
(D)

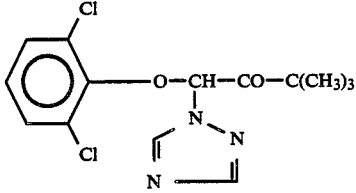
(E)

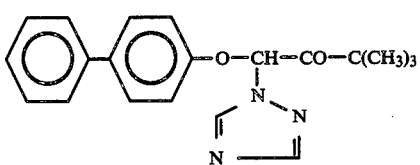
(F)

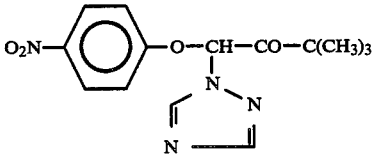
(G)

Example 3

Erysiphe test (barley)/protective/

Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis* f.sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (1), (4), (6), (7), (8), (12), (2), (17), (18), (21), (22) and (29).

Example 4

Erysiphe test (barley)/seed treatment

The active compounds were used as dry dressings. These are prepared by extending the particular active compound with a ground mineral to give a finely pulverulent mixture, which ensured uniform distribution on the seed surface.

To apply the dressing, the seed was shaken with the dressing in a closed glass flask for 3 minutes.

3 batches of 12 grains of the barley were sown 2 cm deep in standard soil. 7 days after sowing, when the young plants had unfolded their first leaf, they were dusted with spores of *Erysiphe graminis* f. sp. hordei.

The plants were placed in a greenhouse at a temperature of about 20° C. and a relative atmospheric humidity of about 80% in order to promote the development of powdery mildew pustules.

Evaluation was carried out 7 days after the inoculation.

In this test, a clearly superior activity compared with the prior art was shown, for example, by the compounds (1), (4), (10) and (2).

Example 5

Sphaerotheca test (cucumber)/protective

Solvent: 4.7 parts by weight of acetone
Emulsifier: 0.3 part by weight alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dripping wet. After the spray coating had dried on, the plants were dusted with conidia of the fungus *Sphaerotheca fuliginea*.

The plants were then placed in a greenhouse at 23° to 24° C. and at a relative atmospheric humidity of about 75%.

Evaluation was carried out 10 days after the inoculation.

In this test, a clearly superior activity compared with the prior art was shown, for example, by the compounds (17) and (21).

It will be understood that the specification and examples are illustrative but not limitative of the present invention and that other embodiments within the spirit and scope of the invention will suggest themselves to those skilled in the art.

We claim:

1. A 3-substituted 1-azolyl-3-methyl-1-phenoxybutan-2-one or -ol of the formula

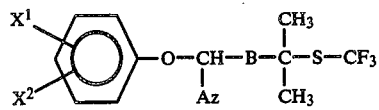

in which
Az represents 1,2,4-triazol-1-yl or imidazol-1-yl,
B represents the keto group or the CH(OH) group,
$X^1$ represents hydrogen, fluorine, chlorine, methyl or phenyl, and
$X^2$ represents hydrogen or chlorine, or a physiologically tolerated acid addition salt or metal salt complex thereof.

2. A salt or complex according to claim 1, which is an addition salt of an acid selected from hydrogen halide acids, phosphoric acid, nitric acid, sulphuric acid, sulphonic acids and monofunctional or bifunctional carboxylic acids, or a complex of a metal salt, the metal of which is copper, zinc, manganese, magnesium, tin, iron or nickel and the anion of which is halide, phosphate, nitrate or sulphate.

3. A compound according to claim 1, wherein such compound is 1-(4-chlorophenoxy)-3-methyl-1-(1,2,4-triazol-1-yl)-3-trifluoromethylthio-butan-2-ol of the formula

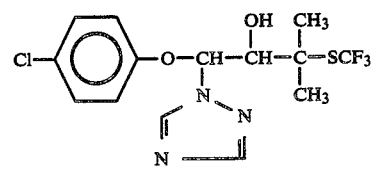

or a physiologically tolerated acid addition salt or metal salt complex thereof.

4. A compound according to claim 1, wherein such compound is 1-(4-chlorophenoxy)-3-methyl-1-(imidazol-1-yl)-3-trifluoromethylthio-butan-2-ol of the formula

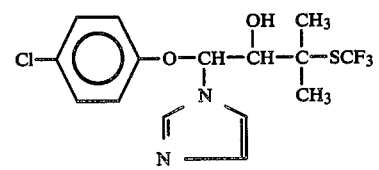

or a physiologically tolerated acid addition salt or metal salt complex thereof.

5. A compound according to claim 1, wherein such compound is 1-(4-chlorophenoxy)-3-methyl-1-(imidazol-1-yl)-3-trifluoromethylthio-butan-2-one of the formula

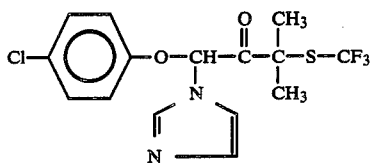

or a physiologically tolerated acid addition salt or metal salt complex thereof.

6. A compound according to claim 1, wherein such compound is 1-(2,4-dichlorophenoxy)-3-methyl-1-(imidazol-1-yl)-3-trifluoromethylthio-butan-2-one of the formula

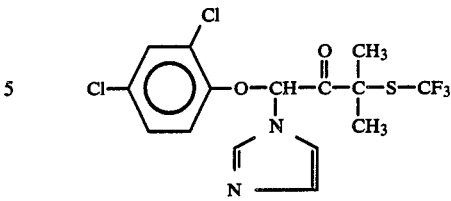

or a physiologically tolerated acid addition salt or metal salt complex thereof.

7. A fungicidal composition comprising a fungicidally effective amount of a compound according to claim 1 in admixture with a diluent.

8. A method of combating fungi comprising applying to the fungi, or to a habitat thereof, a fungicidally effective amount of a compound according to claim 1.

9. The method according to claim 8, wherein such compound is
1-(4-chlorophenoxy)-3-methyl-1-(1,2,4-triazol-1-yl)-3-trifluoromethylthio-butan-2-ol,
1-(4-chlorophenoxy)-3-methyl-1-(imidazol-1-yl)-3-trifluoromethylthio-butan-2-ol,
1-(4-chlorophenoxy)-3-methyl-1-(imidazol-1-yl)-3-trifluoromethylthio-butan-2-one or
1-(2,4-dichlorophenoxy)-3-methyl-1-(imidazol-1-yl)-3-trifluoromethylthio-butan-2-one,
or a physiologically tolerated acid addition salt or metal salt complex thereof.

* * * * *